United States Patent
Jelinek et al.

(10) Patent No.: US 12,108,759 B2
(45) Date of Patent: Oct. 8, 2024

(54) SYNTHESIS OF ANTIMICROBIAL CARBON DOTS AND USES THEREOF

(71) Applicant: B.G. Negev Technologies & Applications Ltd., at Ben-Gurion University, Beer-Sheva (IL)

(72) Inventors: Raz Jelinek, Reut (IL); Sagarika Bhattacharya, Beer-Sheva (IL); Gil Otis, Beer-Sheva (IL)

(73) Assignee: B.G. NEGEV TECHNOLOGIES & APPLICATIONS, LTD., AT BEN-GURION UNIVERSITY, Beer-Sheva (IL)

( * ) Notice: Subject to any disclaimer, the term of this patent is extended or adjusted under 35 U.S.C. 154(b) by 678 days.

(21) Appl. No.: 17/290,910

(22) PCT Filed: Oct. 31, 2019

(86) PCT No.: PCT/IL2019/051189
§ 371 (c)(1),
(2) Date: May 3, 2021

(87) PCT Pub. No.: WO2020/089911
PCT Pub. Date: May 7, 2020

(65) Prior Publication Data
US 2022/0030856 A1 Feb. 3, 2022

Related U.S. Application Data

(60) Provisional application No. 62/755,490, filed on Nov. 4, 2018.

(51) Int. Cl.
A01N 25/26 (2006.01)
A01N 35/10 (2006.01)
G01N 33/58 (2006.01)

(52) U.S. Cl.
CPC ............. *A01N 25/26* (2013.01); *A01N 35/10* (2013.01); *G01N 33/582* (2013.01)

(58) Field of Classification Search
None
See application file for complete search history.

(56) References Cited

PUBLICATIONS

Bhattacharya, S., et al., Nitric Oxide Sensing through Azo-Dye Formation on Carbon Dots, ACS Sens. 2 (2017) pp. 1215-1224. (Year: 2017).*
Gil Otis et al: "Selective Labeling and Growth Inhibition of Pseudomonas aeruginosa by Aminoguanidine Carbon Dots", ACS Infectious Diseases, 5 (2), 292-302, Dec. 27, 2018.
Sagarika Bhattacharya et al: "Nitric Oxide Sensing through Azo-Dye Formation on Carbon Dots", ACS Sensors, 2 (8), 1215-1224, Aug. 3, 2017.

(Continued)

*Primary Examiner* — Dominic Lazaro
(74) *Attorney, Agent, or Firm* — McCormick, Paulding & Huber PLLC

(57) ABSTRACT

The present invention relates to antibacterial carbon dots, having aminoguanidine functionality on their outermost surface. The invention further relates to the synthesis of said antibacterial carbon dots, and to the uses of these carbon dots for inhibiting a biofilm formation in the presence of said carbon dots and as fluorescent labeling markers for specific bacteria.

22 Claims, 8 Drawing Sheets

(56) References Cited

PUBLICATIONS

Margarita Ritenberg et al: "Imaging Pseudomonas aeruginosa Biofilm Extracellular Polymer Scaffolds with Amphiphilic Carbon Dots", ACS Chemical Biology, 11 (5), 1265-1270, May 20, 2016.

Jingjing Yang et al., "Carbon Dot-Based Platform for Simultaneous Bacterial Distinguishment and Antibacterial Applications", ACS Appl. Mater. Interfaces, vol. 8, No. 47, pp. 32170-32181, Oct. 17, 2016.

Zhi-Yu Wei et al "Synthesis and biological evaluation of chalcone derivatives containing aminoguanidine or acylhydrazone moieties", Bioorganic & medicinal chemistry letters 26 (4), 5920-5925, Dec. 31, 2016.

International Search Report for PCT Serial No. PCT/IL2019/051189 dated Jan. 13, 2020.

Sagarika Bhattacharya et al., "Carbon-dot-hydrogel for enzyme-mediated bacterial detection," RSC Adv., vol. 7, No. 2, pp. 588-594, Jan. 3, 2017.

Sukhendu Nandi et al., "Bacterial detection with amphiphilic carbon dots," Analyst, vol. 140, No. 12, pp. 4232-4237, Apr. 13, 2015.

Xian-Wu Hua et al., "Bacteria-derived fluorescent carbon dots for microbial live/dead differentiation," Nanoscale, vol. 9, No. 6, pp. 2150-2161, Feb. 14, 2017.

Junjun Liu et al., "One-step hydrothermal synthesis of photoluminescent carbon nanodots with selective antibacterial activity against Porphyromonas gingivalis," Nanoscale, vol. 21, pp. 7135-7142, Apr. 20, 2017.

Travlou, Nikolina A., et al., "S- and N-doped 1-15 carbon quantum dots: Surface chemistry dependent antibacterial activity", Carbon, Elsvier Oxford, GB, vol. 135, Apr. 12, 2018 (Apr. 12, 2018), pp. 104-111, XP085408000, ISSN: 0008-6223, DOI: 10.1016/J.CARBON. 2018.04.018 * abstract *.

Dong, Xiuli et al., "Antibacterial effects of carbon dots in combination with other antimicrobial reagents", PLOS ONE, vol. 12, No. 9, Jul. 21, 2017 (Jul. 21, 2017), p. e0185324, XP055959274, DOI: 10.1371/journal.pone.0185324 Retrieved from the Internet: URL: https://journals.plos.org/plosone/article/file?id=10.1371/journal.pone. 0185324&type=printable>.

Jijie, Roxana et al., "Enhanced antibacterial activity of carbon dots functionalized with ampicillin combined with visible light triggered photodynamic effects", Colloids and Surfaces B: Biointerfaces, Elsevier Amsterdam, NL. vol. 170, Jun. 19, 2018 *Jun. 19, 2018), pp. 347-354, XP085458775, ISSN: 0927-7765, DOI: 10.1016/J. COLSURFB.2018.06.040.

Extended European Search Report corresponding to European Patent Application No. 19878213.8 dated Sep. 23, 2022.

* cited by examiner

Increasing AG-C-dots concentration

SYNTHESIS OF ANTIMICROBIAL CARBON DOTS AND USES THEREOF

CROSS-REFERENCE TO RELATED APPLICATIONS

This application is a National Stage application of International Patent Application No. PCT/IL2019/051189, filed on Oct. 31, 2019, which claims priority to U.S. Patent Application No. 62/755,490, filed on Nov. 4, 2018 each of which is hereby incorporated by reference in its entirety.

TECHNICAL FIELD

In recent years the ability of bacteria to develop resistance to commonly used antibacterial materials has been studied. Different approaches are being constantly developed in order to overcome the adverse phenomenon of multi drug resistant (MDR) bacteria.

Various antibacterial materials such as novel antibiotics, antimicrobial peptides (AMPs), metallic based nanoparticles (NPs), and others have been employed as inhibitors and antibacterial substances. It is well-known that metallic NPs, especially silvers-based NPs, possess antibacterial properties. However, silver-based NPs, as well as other inorganic NPs, were shown to be toxic and exhibited collateral damage to the host cells and to the natural flora in humans and were not selectively lethal to the desired bacterial cells.

The importance of biocompatibility combined with the advantageous use of NPs as antimicrobial substances lead to harnessing carbon dots (C-dots) as antimicrobial carriers. Carbon dots are a relatively new class of carbon nanomaterials, generally characterized in having a diameter of less than 10 nm. C-dots exhibit remarkable physico-chemical properties, including tunable fluorescence, low photo-bleaching, and desired biocompatibility. C-dots have been employed in diverse applications, including chemical and biological sensing, optics, catalysis, and others. Importantly, C-dots can be essentially synthesized from any carbonaceous precursors, they are generally non-toxic and environmentally-friendly; as such, C-dots have attracted significant interest as vehicles for biological and biomedical applications, including bioimaging, drug delivery and targeting, and therapeutics.

Recently, the use of C-dots as fluorescent probes for bacterial detection and labelling were disclosed (S. Bhattacharya, S. Nandi, and R. Jelinek, *RSC Adv.*, vol. 7, no. 2, pp. 588-594, 2017, S. Nandi, M. Ritenberg, and R. Jelinek, *Analyst*, vol. 140, no. 12, pp. 4232-4237, 2015). Additionally, bacterial biofilm staining and bacterial viability testing were disclosed (X. W. Hua, Y. W. Bao, H. Y. Wang, Z. Chen, and F. G. Wu, *Nanoscale*, vol. 9, no. 6, pp. 2150-2161, 2017). C-dots directed against Gram-positive bacteria have been disclosed (J. Yang et al., *ACS Appl. Mater. Interfaces*, vol. 8, no. 47, pp. 32170-32181, 2016), and antibacterial activity against *Porphyromonas gingivalis*, an anaerobic Gram-negative pathogen was reported (J. Liu et al., N *Nanoscale*, vol. 21, pp. 7135-7142, 2017). However, currently employed synthetic pathways mostly pursued in such systems are focusing on conjugating as-prepared C-dots with bacterial targeting agents. These strategies have shown certain limitations and often involve multi-step production pathway and a complex synthetic methodology which lead to insufficient selectivity and low yield.

Thus, there is still a need for a straightforward, environmentally friendly synthetical approach allowing the production of biocompatible C-dots, exhibiting advantageous antimicrobial properties while being selective towards the desired bacterial source.

SUMMARY

Selective antimicrobial agents which are both biocompatible and easy to synthesize are hard to come by. The present invention provides an advantageous antimicrobial carbon dots (C-dots), having aminoguanidine on their surface, which are selective towards *P. aeruginosa* cells. The C-dots of the invention presenting the aminoguanidine functionality on their surface in a localized and tightly bounds manner, which contributes to the antimicrobial activity of said C-dots. The C-dots of the invention are being synthesized by reacting an aminoguanidine precursor and a further carbonaceous source, which may be selected from the groups of carboxylic acids, sugars, amino acids, peptides and other carbon-based natural materials.

It was surprisingly found that the synthetic pathway, and more specifically, the exact mass ratio between the reagents forming the aminoguanidine decorated C-dots of the invention has a crucial effect on the antimicrobial properties of the C-dots achieved from said synthesis. Thus, the present invention provides a method for preparing antimicrobial C-dots characterized in having at least one aminoguanidine functional group on their outer surface, wherein said method comprising the step of reacting a carbonaceous molecule with aminoguanidine precursor under heating, further wherein the mass ratio between aminoguanidine precursor and carbonaceous molecule is between about 1:2 to about 3.85:1, or between about 2.5:1 to about 1.5:1. In some currently preferred embodiments, the mass ratio between aminoguanidine precursor and the carbonaceous molecule is about 2:1. In some specific embodiments, the carbonaceous molecule is citric acid and the aminoguanidine precursor is aminoguanidine hydrochloride.

The present invention provides antimicrobial carbon-dots (C-dots) characterized in having at least one aminoguanidine functional group on their outer surface, wherein said C-dots are characterized in having a maximal emission at a wavelength of about 480 nm upon excitation at a wavelength of 390 nm, i.e. the C-dots of the inventions' fluorescence is in the UV-visible range of the spectrum, therefore, can be conveniently utilized for fluorescent labeling. The zeta potential of the C-dots according to the present invention is related to the advantageous antimicrobial properties of said C-dots. Thus, the C-dots of the invention are characterized by having a zeta potential value higher than about −16 mV in pH=7.4, or a zeta potential between −1 to −15 mV in pH=7.4. In some currently preferred embodiments, the zeta potential of the C-dots of the invention is between about −1 to about −10 mV. In some specific embodiments the zeta potential of the C-dots of the invention is about −2 mV.

In another aspect, the present invention provides a method for inhibiting the formation of a biofilm and/or disrupting the propagation of a biofilm comprising contacting antimicrobial C-dots having at least one aminoguanidine functional group on their outer surface with biofilm forming bacterial cells and/or an existing biofilm sought to be extinguished.

The present invention further provides a method for selective bacterial cell labeling, comprising the steps of A) contacting bacterial cells sought to be labeled with C-dots having at least one aminoguanidine functional group on their outer surface at a concentration range of about 0.1 mg/ml to about 1 mg/ml; and B) removing excess C-dots; thereby providing precise labeling.

DETAILED DESCRIPTION

In one aspect, the present invention provides antibacterial carbon dots (C-dots) which are characterized by having aminoguanidine functionality on their outer surface. The aminoguanidine chemical groups are situated on the C-dot surface and constitute an integral part of the C-dot structure, obtained by a facile synthetic approach. Thus, there is no need to further functionalize the surface of the C-dots or exchange surface ligands with other active antibacterial agents or bacterial targeting agents. According to the principles of the invention, the antimicrobial C-dots are characterized in a zeta potential value higher than about −16 mV in pH=7.4. In some embodiment, the zeta potential is between −1 to −15 mV in pH=7.4. In some other embodiments, the zeta potential is between −1 to −10 mV in pH=7.4. In some specific embodiments, the zeta potential of the C-dots of the invention is about −2 mV. Without being bound by any mechanism or theory, it is postulated that the negative but relatively neutral zeta potential of the C-dots of the invention is related to improved antibacterial properties. For example, as can be seen in FIG. 7, the zeta potential of C-dots synthesized with a ratio of 4:1 aminoguanidine precursor to citric acid have a more negative zeta potential than that of C-dots prepared with a ratio of 2:1 aminoguanidine precursor to citric acid. The great difference in antibacterial functionality can be seen in FIGS. 6 B and C, where in FIG. 6B the 2:1 C-dots of the invention gave rise to a superb antibacterial effect while in FIG. 6C the 4:1 C-dots do not show a significant antibacterial effect in *Pseudomonas aeruginosa* PAO 1 luxCDABE.

In some embodiments, the antimicrobial activity of the C-dots of the invention presents upon growing the bacterial cells in the presence of said C-dots. In some embodiments, the antimicrobial activity of the C-dots of the invention can be attributed to the display of aminoguanidine groups in a localized manner on the C-dot surface. Without being bound by any theory or mechanism of action, it is postulated that the localization of the aminoguanidine groups on the C-dot surface generates a certain "effective concentration" of said groups, which in turn demonstrates an improved antimicrobial activity compared with non-bound aminoguanidine groups. In some related embodiments, the C-dots of the invention are selective in their antimicrobial activity towards *P. aeruginosa* cells. In some embodiments, the antibacterial C-dots physically attach to the bacterial surface. In some embodiment said attachment may be via electrostatic interaction of said C-dots to certain regimes on the bacterial cell membrane. In some embodiments, the C-dots of the invention attach electrostatically to the LPS component in the bacterial membrane.

In some related embodiments, the C-dots of the invention are characterized in having a maximal emission at about 480 nm upon excitation at 390 nm. The term 'maximal emission' refers to the highest fluorescence value of a material. This value is measured by systematic excitation of the material under examination at different wavelengths and measuring the emission spectra at each excitation wavelength. In the present invention, the fluorescence of the c-dots of the invention was measured in aqueous media, and the highest fluorescence value was obtained upon excitation at 390 nm, and the corresponding emission was measure at about 480 nm.

In other embodiments, the antimicrobial C-dots as described above are characterized by having a diameter of between about 3.5 to about 5 nm. In some embodiments, the antimicrobial C-dots of the invention are characterized by having an XPS spectrums as demonstrated in FIG. 1D.

In another aspect, the present invention provides a method for disrupting the propagation of a biofilm, comprising contacting the antimicrobial C-dots of the invention with said biofilm. In some currently preferred embodiments, said biofilm is a *P. aeruginosa* biofilm. In some related embodiments, the MIC50 of C-dots of the invention is ranging between about 0.1 mg/ml and 0.5 mg/ml. The term "MIC50" as it appears herein and in the claims refers to the minimum concentration of the antimicrobial C-dots which is required for inhibiting 50% of the bacterial cell growth. The term "LPS" as used herein and in the claims refers to lipopolysaccharide, a natural component of the outer membrane of Gram negative bacteria. In some other embodiments, the C-dots are being inserted into the bacterial cell.

In some embodiments, the C-dots of the invention are useful for anti-microbial purposes. In some related embodiments, the C-dots of the invention may be deposited onto a surface, such as a plastic-based or ceramic-based surfaces, by spreading an aqueous solution comprising an effective amount of the C-dots of the invention onto the surface sought to be coated. In some embodiments, applying said C-dots on a surface inhibits a biofilm formation on said surface. The term 'effective amount of C-dots' as used herein and in the claims refers to the concentration of C-dots which is required in order to inhibit the formation of a biofilm on the surface, said concentration is based on the MIC50 dose of said particles as measured in Example 2, and may vary with surface dimensions and smoothness. It is postulated that a man skilled in the art given the MIC50 dose will be able to optimize the required C-dot concentration according to the properties of the surface sought to be coated. According to the principles of the invention, *P. aeruginosa* bacteria proliferation is inhibited by contacting said coated surface. It was further shown that upon contacting a solution comprising *P. aeruginosa* bacteria of $O.D_{600}$. 0.05 with an agar substrate comprising 1 mg/mL of aminoguanidine-citric acid dots (AG-CA-dots) of the invention, the biofilm formation was inhibited, compared to a similar system comprising no AG-CA-dots in/on the surface, as demonstrated in the Examples herein below.

In another aspect, the present invention provides a method for selective labeling of bacteria cells utilizing the antimicrobial C-dots of the invention. The method for selective bacteria cell labeling comprising the following steps: A) contacting the bacterial cells with the C-dots of the invention at a concentration range of between 0.1 to 1 mg/ml for a time duration of preferably less than 10 hours; B) removing excess C-dot via rinsing thereby providing precise imaging. In some embodiments, the concentration of the bacteria suitable for labeling is ranging between about $O.D_{600}$ 0.1 to about 1. In some embodiments, the duration of step A is between about one hour to about 5 hours. In some embodiments, the duration of step A is about 3 hours. In some embodiments, the selective labeling utilizing the C-dots of the invention is specific towards *P. aeruginosa* cells, allowing to differentiate them from other bacterial cells, and can serve for imaging purposes utilizing different microscopy techniques. In some related embodiments, said labeling is carried out by the physical attachment of the C-dots of the invention to the surface of certain bacterial cells in a selective manner. In some embodiments, the selective labeling utilizing the C-dots of the invention can be useful for diagnostic purposes. Such labeling can be carried out for example, by providing a bacterial pellet sample sought to be diagnosed, suspending the pellet in a solution of 1 mg/mL amino guanidine C-dots of the invention dissolved in PBS buffer. The resulting solution is incubated for a about 2-3 hours in 37° C., and later on the bacterial pellet is washed with PBS buffer in order to discard C-dots that were not attached to the bacterial cells. After final washing, the bacterial cells are imaged and the C-dot-labelled bacterial cells can be easily detected utilizing for example, confocal laser scanning microscopy (CLSM).

In another aspect, the present invention provides a facile synthetic route for the preparation of antimicrobial C-dots of the invention, utilizing a hydrothermal reaction. According to the principles of the invention, the unique ratio between aminoguanidine precursor and a further carbonaceous source, e.g. citric acid, have a crucial effect on the antibacterial activity presented by the resultant C-dots. It is to be understood that the aminoguanidine groups concentration on the C-dot surface is a direct result of the ratio between the components used in the synthesis and said concentration effects the desired outcome of antibacterial activity of the resultant C-dots. According to some embodiments, the carbonaceous source utilized for the synthesis is selected from the group consisting of carboxylic acids, sugars, amino acids, ascorbic acid, peptides and other carbon-based natural materials. According to some currently preferred embodiments, the further carbonaceous source utilized for the synthesis is citric acid. In some related embodiments, the molar ratio between aminoguanidine precursor and citric acid is between about 1:2 to about 3.85:1. In some related embodiments, the molar ratio between aminoguanidine precursor and citric acid is between about 1:2 to about 3.5:1. In some other embodiments, the molar ratio between aminoguanidine precursor and citric acid is between about 1.5:1 to about 2.5:1. In some specific embodiments, the molar ratio between aminoguanidine precursor and citric acid is about 2:1. Thus, the present invention provides a method for preparing antimicrobial C-dots characterized in having at least one aminoguanidine functional group on their outer surface, wherein said method comprising the step of reacting a carbonaceous molecule with aminoguanidine precursor in aqueous media under heating. In some embodiments the abovementioned heating is taking place at a temperature range of between about 85 to about 250° C. In some other embodiments, the heating is carried out at a range of between 100 to about 200° C. In some embodiments, the heating is carried out to a temperature of about 150° C. In some embodiments, the duration of the reaction under heating is between about 1 to about 5 hours. In some currently preferred embodiments, said reaction's duration is about 2 hours. The aminoguanidine decorated C-dots obtained from the above mentioned synthesis are usually washed in order to remove unwanted impurities, and often dialyzed in aqueous media for further processing or use. According to the principles of the invention, the obtained C-dots may be used in their dry form as well as in a suspension form (in solution). The term 'carbonaceous molecule' and the term 'carbonaceous source' as appear herein are interchangeable and refer to carbon based compounds selected from the group consisting of carboxylic acids, sugars, amino acids, ascorbic acid and peptides. In some currently preferred embodiments, the carbon based compound is a carboxylic acid. In some related embodiments, the carbon based compound is selected from ascorbic acid, aspartic acid, glutamic acid and citric acid. In some currently preferred embodiments, the carbonaceous molecule is citric acid.

The term 'AG-CA-dots' is interchangeable with the term 'AG-C dots' and refers to C-dots presenting at least one aminoguanidine group on their surface. The AG-C dots of the invention were synthesized with the specific ratio of aminoguanidine precursor and citric acid between ranging from about 1:2 to about 3.85:1. In some currently preferred embodiments the ratio is between about 1.5:1 to about 2.5:1 or about 2:1 of aminoguanidine precursor and citric acid, respectively.

The term 'localized' and the term 'tightly bound' as appear herein and in the claims are both referring to the aminoguanidine moieties situated on the outer surface of the C-dots of the invention. The fact that the aminoguanidine moieties are not free flowing in the solution but bound to a small surface (concentrated on a nano-size particle) increases the efficacy of said aminoguanidine towards bacterial cells.

C. together with the AG-C-dots. Red squares represent bacterial viability and black dots represent % nitrogen B. Growth curves of *Pseudomonas aeruginosa* PAO 1 luxCD-ABE in the presence of the AG-C-dots prepared at different mass ratios. Black: control, Red: AG:CA 2:1, Blue: AG:CA 1:1, Green: AG:CA 1:2, Pink: free aminoguanidine C. Growth curves of *Pseudomonas aeruginosa* PAO 1 luxCD-ABE in the presence of the AG-C-dots prepared at 4:1 mass ratios (Red) vs control (Black). C-dot concentrations were 1 mg/mL.

Figure 7:
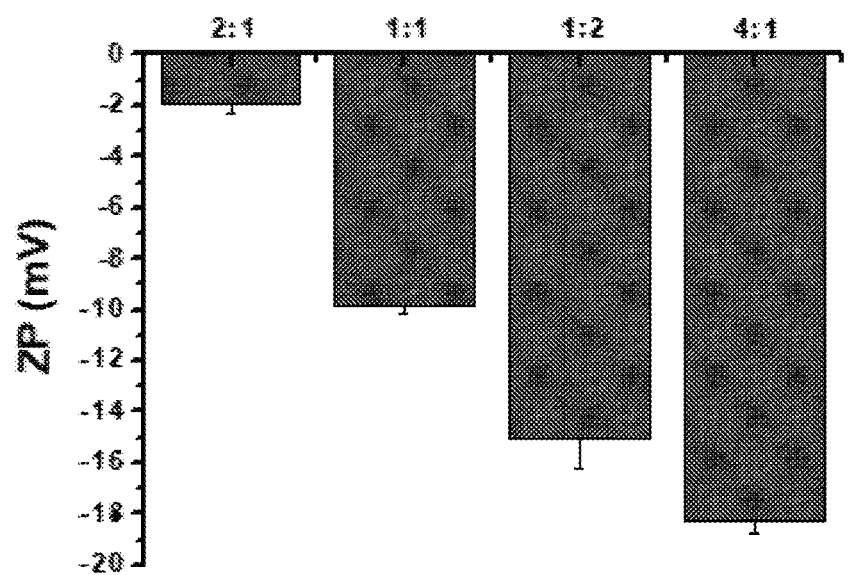

FIG. 7: Surface charges of the C-dots as measured in zeta potential measurements. Zeta potential of different C-dots having varied AG:CA ratios measured in PBS buffer pH=7.4.

EXAMPLES

Example 1—Synthesis of Antibacterial C-Dots

Antimicrobial carbon dots were prepared using aminoguanidine (AG) and citric acid (CA) precursors. Specifically, AG:CA (2:1) C-dots were prepared by hydrothermal synthesis: 50 mg aminoguanidine hydrochloride 98% was mixed with 25 mg citric acid and dissolved in 200 µL of distilled water. The solution was tightly sealed using a Teflon film and then heated in an oven to 150° C. for 2 hours. After the reaction was completed, the resultant mixture was allowed to cool to room temperature yielding a brown precipitate indicating the formation of carbon dots, the precipitate was re-dispersed in 2 mL methanol through sonication for 2 minutes and centrifuged at 10,000 rpm for 10 min to remove high-weight precipitate and agglomerated particles. After this, methanol was evaporated under reduced pressure to obtain an orange color solid. The solid obtained was dialyzed (MWCO 2000) against distilled water for 24 hours, after complete purification, the clear orange carbon dots solution was taken for further characterization and use.

Other C-dots were obtained utilizing an identical synthetic procedure, utilizing different weight ratios of the aminoguanidine (AG) and citric acid (CA) precursors in order to validate the effect of the unique ratio of precursors on the resultant antibacterial activity of the C-dots produced. (I) AG-CA (1:1) C-dots were prepared by using 50 mg AG and 50 mg CA; (II) AG:CA (1:2) C-dots by using 25 mg AG/50 mg CA; and (III) AG:CA (4:1) C-dots by using 60 mg AG/15 mg CA.

Physical characterization of antimicrobial C-dots as prepared in section A: the quantum yield (QY) of the AG-C-dots in deionized water was determined by placing the C-dots inside a quartz cuvette and the integrated photoluminescence intensity (in the range of 380-650 nm) was measured upon excitation at 350 nm. The absorbance values of the C-dots at 350 nm were measured as well with respect to a standard solution of quinine sulfate dissolved in 0.2N $H_2SO_4$ ($\Phi$=58).

Finally, quantum yield of each C-dots solution was calculated using the equation:

$$\Phi_{sm} = \Phi_{st} \times \left(\frac{Pl_{sm}}{Abs_{sm}}\right) \times \left(\frac{Abs_{st}}{Pl_{st}}\right) \times \left(\frac{\eta_{sm}^2}{\eta_{st}^2}\right)$$

where $\Phi$=quantum yield, Pl=integrated photoluminescence, Abs=absorbance at $\lambda_{ext}$, $\eta$=refractive index of the solvent, st=quinine sulfate standard and sm=C-dots sample. The quantum yield of the AG-C-dots of the invention was approximately 3% in deionized water.

Figure 1A:
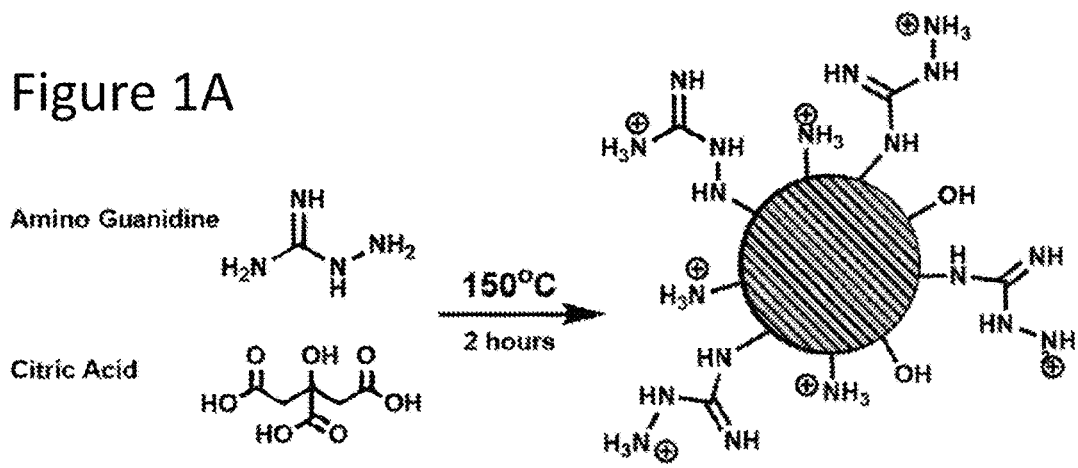
FIG. 1: A. Synthetic scheme, showing the one-pot hydrothermal route generating AG-C-dots from a mixture of AG and citric acid. B. Excitation-dependent fluorescence emission spectra of the AG-C-dots; different excitation wavelengths are indicated 350 nm Black, 370 nm Red, 390 nm Blue, 410 nm Green, 430 nm Pink, 450 nm Brown. C. High resolution transmission electron microscopy (HR-TEM) image of AG-C-dots. D. Deconvoluted C 1s and N 1s x-ray photoelectron spectra (XPS) of the AG-C-dots; the functional units are indicated.
Figure 1B:
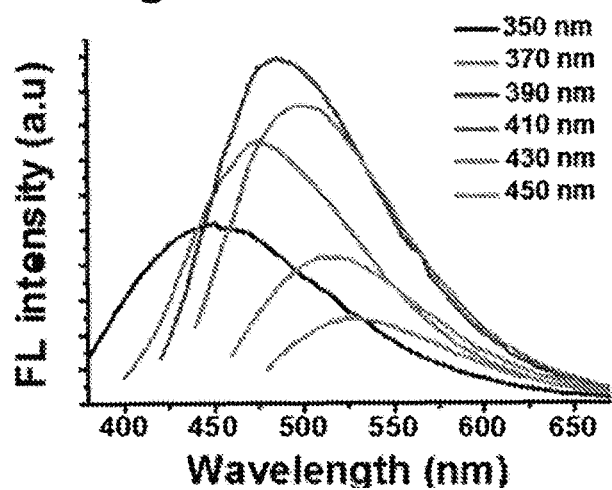
Figure 1C:
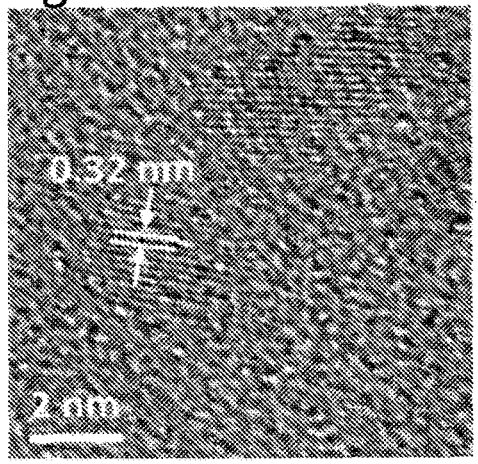

Fluorescence spectroscopy. AG-C-dot solutions in deionized water were placed inside quartz cuvettes and the fluorescence emission spectra were recorded on an FL920 spectrofluorimeter (Edinburgh Instruments, UK). The AG-C-dots exhibited the typical excitation-dependent emission spectra (FIG. 1B) with the maximal emission (upon excitation at 390 nm) at 480 nm (i.e. green-yellow appearance).

High Resolution Transmission Electron Microscopy (HR-TEM). The AG-C-dots solution was placed upon a graphene-coated copper grid and HR-TEM images were recorded on a 200 kV JEOL JEM-2100F microscope (Tokyo, Japan). The sample was dried overnight before the measurement. Size distribution of the AG-C-dots, determined by the HR-TEM analysis, gave rise to 4.3+/−0.5 nm.

X-ray Photoelectron Spectroscopy (XPS). The AG-C-dot solution was placed upon a silicon wafer and dried overnight. Once dried, the samples were measured using an X-ray photoelectron spectrometer type ESCALAB 250 ultrahigh vacuum (1×10-9 bar) apparatus fitted with an Al Kα X-ray source and a monochromator. The beam diameter was 500 µm with pass energy (PE) of 150 eV for recording survey spectra, while for high energy resolution spectra the recorded pass energy (PE) was 20 eV. The AVANTAGE program was used to process the XPS results.

Figure 1D:
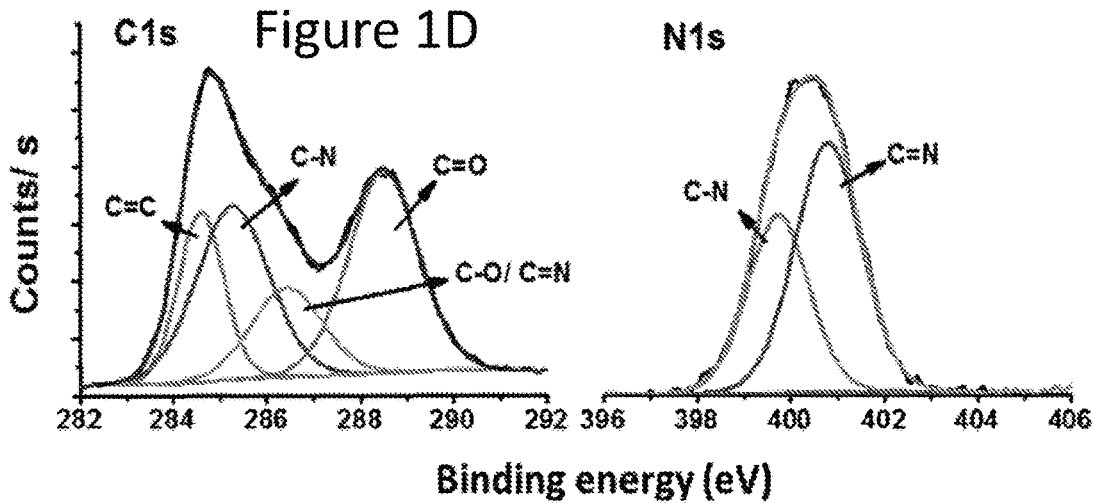

X ray photoelectron spectroscopy (XPS) data is depicted in FIG. 1D. According to the results one can see the functional units on the AG-C-dots' surface, confirming retention of the aminoguanidine and carboxylic acid residues. Specifically, the C 1s spectrum in FIG. 1D features deconvoluted peaks at 284 eV, 285.2 eV, 286.5 eV, and 288.5 eV which correspond to C=C, C—N, C—O/C=N, and C=O bonds, respectively. The N is XPS peak in FIG. 1D similarly displays deconvoluted signals at 399.7 eV and 400.7 eV ascribed to the C—N and C=N bonds, respectably.

Zeta potential. C-dot solutions in PBS buffer (pH=7.4) were placed inside of a Malvern DTS 1070 disposable capillary cuvette and the zeta potential was measured by Zetasizer Nano ZS, Malvern, Worcestershire.

The results are depicted in FIG. 7 for the comparison of different C-dots having distinct aminoguanidine: citric acid precursor ratio, as measured in PBS buffer. It can be seen that the 2:1 C-dots of the invention have relatively neutral surface charge compared to other precursor ratio dots. The measured values of 4:1 C-dots gave rise to a negatively charged particles having a surface charge of about −18 mV in PBS buffer pH=7.4. In comparison, the 2:1 C-dots gave rise to a light surface charge of −2 mV due to a lower excess of amino groups which was mostly neutralized by negatively charged carboxyl groups.

Example 2—Antibacterial Activity

Bacterial growth: Two Gram positive bacterial strains—*Staphylococcus aureus* (*S. aureus*) and *Bacillus cereus* (*B. cereus*) and five Gram negative bacterial strains *Escherichia coli* K12 (*E. coli* K12), *Salmonella enteritidis* (*S. enteritidis*), *Salmonella typhimurium* strain ATCC14028 (*S. typhimurium*), *Pseudomonas aeruginosa* PAO 1 luxCDABE and *Pseudomonas aeruginosa* PAO 1 were used.

*B. cereus* were grown in a brain heart infusion (BHI) medium containing 7.7 gr calf brains (infusion from 200 gr), 9.8 beef heart (infusion from 250 gr), 10 gr protease peptone, 2 gr dextrose, 5 gr sodium chloride and 2.5 gr disodium phosphate per 1 liter medium. The bacteria was grown in 30

C for 12 hours, all the rest of the bacterial species were grown in Lennox medium containing 10 gr Tryptone, 5 gr yeast extract and 5 gr sodium chloride per 1 liter medium. The bacteria were grown for 12 hours at 37° C.

The antibacterial activity of AG-C-dots was evaluated using a broth dilution assay in which the bacteria were initially grown in medium overnight until full growth was achieved (O. $D_{600}$=1), followed by dilution of the bacteria to $O.D_{600}$=0.05 (CFU=1×10$^6$) and were incubated with AG-C-dots in different concentrations (1, 0.5, 0.25, 0.125, 0.0625 mg/mL), growth curves describing the change in $O.D_{600}$ with time were collected for 24 hours of incubation at 37° C. The growth curves were measured in 96-well plates on a Biotek Synergy H1 plate reader (Biotek, Winooski, VT, USA).

B) The MIC50 values referring to the concentrations in which the bacterial cell viability was 50% after 24 hours incubation with C-dots, were determined using a broth dilution method. All bacterial cells were grown in optimum growth conditions with increasing concentrations of C-dots in the medium. $O.D_{600}$ values were taken after 24 hours of incubation and the C-dot concentrations in which the bacterial viability was reduced to 50% were determined.

C) Inhibition on agar plates containing different concentrations of C-dots as prepared in section 1A were prepared by initially autoclaving L.B agar, after cooling the agar to approximately 60 C dry C-dots powder was added to the warm agar and diluted in order to create the following dilution series: 0.0625, 0.125, 0.25, 0.5 and 1 mg/mL, the agar plates were than left to cool down and harden for further use.

After hardening, 2 microliters of P. aeruginosa solution ($O.D_{600}$=1) was placed on each agar plate and the agar plates were incubated for 8 hours in 37° C.

D) Scanning electron microscopy (SEM). Bacterial solutions at $O.D_{600}$=0.05 were incubated together with AG-C-dots for 12 hours at 37 C, following which the bacterial pellet was collected and washed several times with PBS buffer (0.01 M phosphate buffer, 0.0027 M potassium chloride, 0.137 M sodium chloride, pH=7.4). Subsequently, the bacteria were re-suspended in PBS buffer and fixated for the SEM experiments. Bacterial strains were fixed upon a Poly-L-lysine cover glass, initially using glutaraldehyde 2.5% solution in buffer for 2 hours, then incubated with osmium tetroxide 1% solution, followed by dehydration by rinsing with ethanol/HMDS mixtures. The fixed bacteria were spray-coated with a thin gold layer and placed in the microscope for measurements. SEM images were recorded using a JSM-7400 SEM (JEOL LTD, Tokyo, Japan).

Results

Figure 2A:
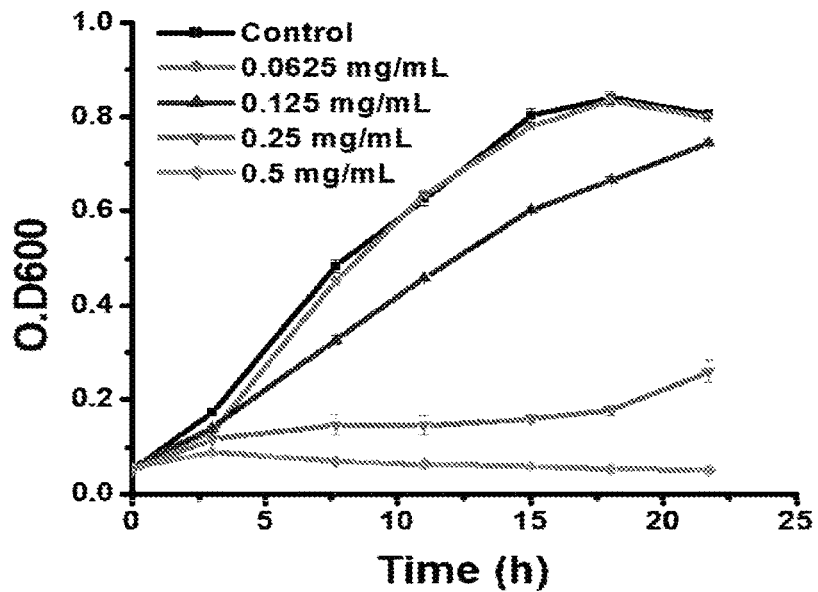
FIG. 2. Antibacterial activities of the aminoguanidine-C-dots. A. Growth curves of *Pseudomonas aeruginosa* PAO 1 luxCDABE recorded through the broth dilution method in different concentration AG-C-dots of the invention (AG:CA is 2:1). B. bacterial viabilities of different strains as a function of AG-C-dots concentrations upon incubation for 18 hours. Color code for both A and B: (black)—control, (red)—0.0625 mg/mL, (blue)—0.125 mg/mL, (green)—0.25 mg/mL, (pink)—0.5 mg/mL C. agar dilution method representing the growth of *P. aeruginosa* PAO 1 luxCDABE in different AG-C-dots (2:1) concentrations. I—control, II—0.0625 mg/mL, III—0.125 mg/mL, IV—0.25 mg/mL, V—0.5 mg/mL.

Antibacterial effects of AG-C-dots. FIG. 2 illustrates the selective antibacterial properties of the AG-C-dots. In the experiments summarized in FIG. 2, AG-C-dots were added to the bacterial growth medium and bacterial proliferation was monitored. The concentration-dependent bactericidal effects of the AG-C-dots against P. aeruginosa PAO 1 luxCDABE are depicted in FIG. 2A, demonstrating that the proliferation of P. aeruginosa PAO 1 luxCDABE was inhibited upon increasing C-dot concentration. No bacterial growth was apparent at a C-dot concentration of 0.5 mg/mL (FIG. 2A). Concentration-dependent anti-bacterial effect against P. aeruginosa PAO 1 luxCDABE was also apparent in the agar dilution method, in which the AG-C-dots were incorporated within the agar matrix (FIG. 2 C).

Figure 2B:
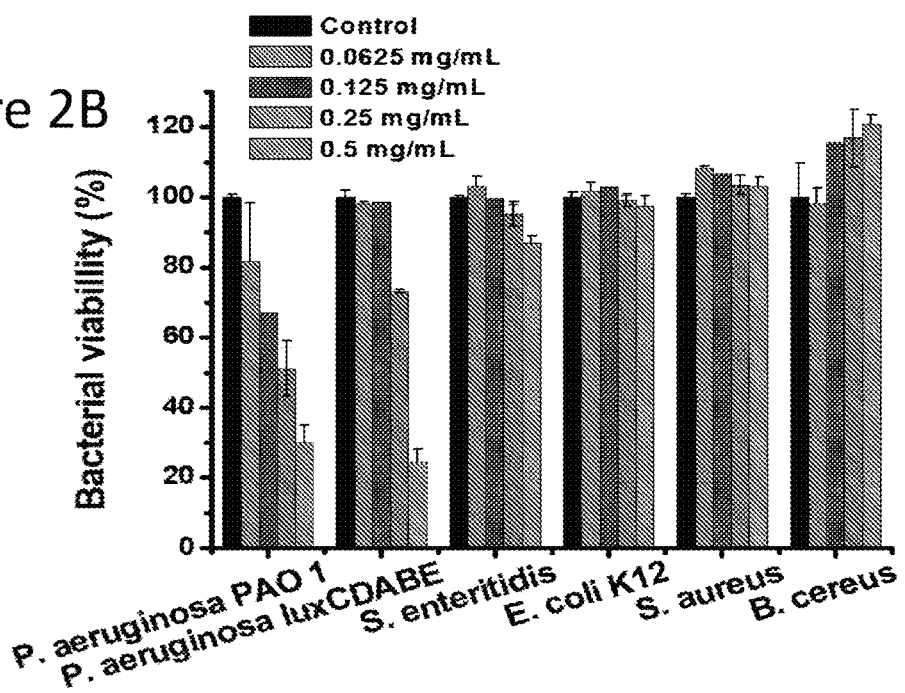
Figure 2C:
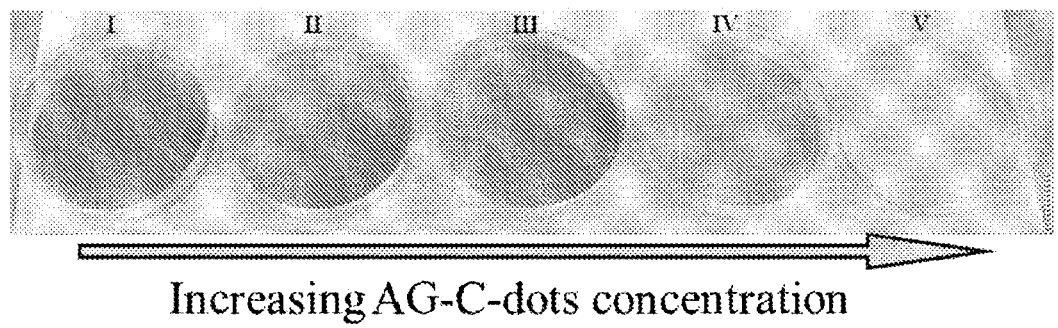

The bar diagram in FIG. 2B demonstrates that the antibacterial effect of AG-C-dots is selective towards P. aeruginosa sp. FIG. 2B demonstrates that the AG-C-dots had significant inhibitory effect upon P. aeruginosa PAO 1 luxCDABE and P. aeruginosa PAO1, while the C-dots appeared to exhibit no antibactericidal effects in case of Salmonella enteritidis, Staphylococcus aureus, E. coli K12 or Bacillus cereus (FIG. 2B).

Table 1 summarizes the minimum concentrations required for inhibiting 50% cell growth (MIC50), further demonstrating the bactericidal selectivity of the AG-C-dots towards P. aeruginosa bacterial strains.

TABLE 1

| Species | Gram type | MIC50 (mg/mL) |
|---|---|---|
| P. aeruginosa PAO 1 luxCDABE | − | 0.156 |
| P. aeruginosa PAO 1 | − | 0.335 |
| S. enteritidis | − | >1 |
| S. typhimurium | − | >1 |
| E. coli K12 | − | >1 |
| B. cereus | + | >1 |
| S. aureus | + | >1 |

Figure 3A:
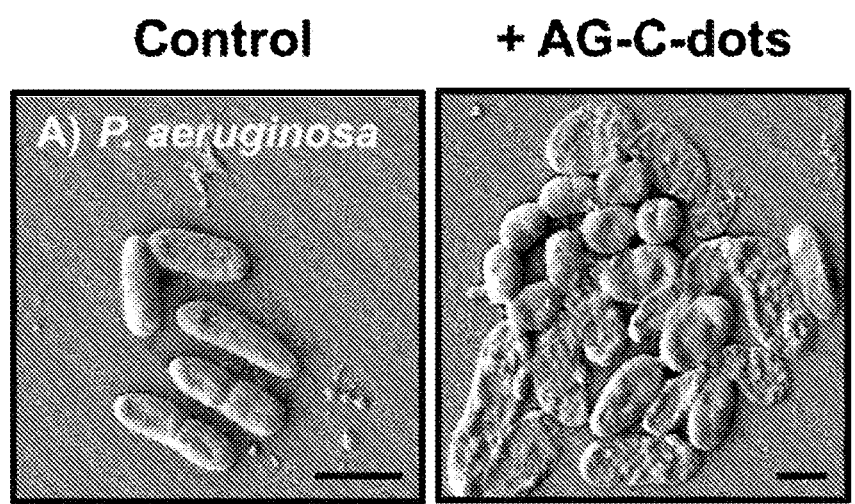
FIG. 3: Effects of aminoguanidine-C-dots upon bacterial cell morphology. Scanning electron microscopy (SEM) images of *Pseudomonas aeruginosa* PAO 1 luxCDABE and *Staphylococcus aureus* incubated with AG-C-dots (0.5 mg/mL) for 12 hours. Scale bars correspond to 1 µm.
Figure 3B:
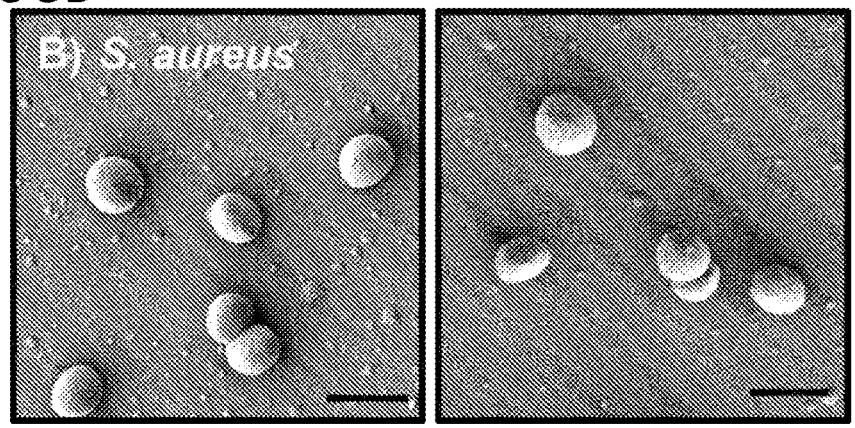

FIG. 3 presents scanning electron microscopy (SEM) images showing the effect of the AG-C-dots upon different bacterial cells. Notably, FIG. 3 reveals that significant morphology alteration occurred when P. aeruginosa PAO 1 luxCDABE cells were incubated with the AG-C-dots, specifically "flattening" and elimination of cell surface smoothness (FIG. 3A). This observation likely indicates leakage of intracellular fluid due to bacterial cell wall permeability induced by the AG-C-dots. In contrast to the severe morphology transformation of the P. aeruginosa PAO 1 luxCDABE cells following incubation with the AG-C-dots, the SEM images in FIG. 3B show no discernable effect of the AG-C-dots upon S. aureus cells, consistent with the data in FIG. 2B and Table 1, pointing to no antibacterial activity of the AG-C-dots against Gram-positive type bacteria.

Figure 6A:
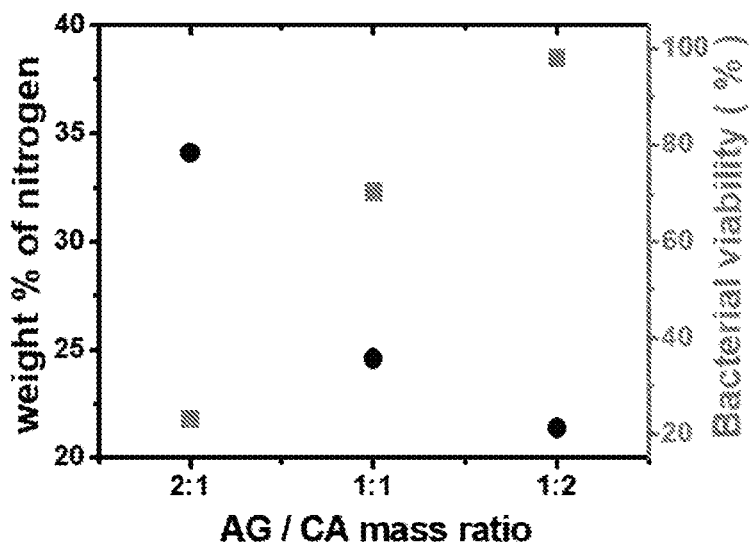
FIG. 6: Surface properties and antibacterial activities of C-dots prepared from the aminoguanidine (AG) and citric acid (CA) precursors at different mass ratios. A. Weight percentage of nitrogen in the AG-C-dots determined by elemental analysis in relation to bacterial cell viability of *P. aeruginosa* PAO 1 luxCDABE after 18 hours growth at 37°
Figure 6B:
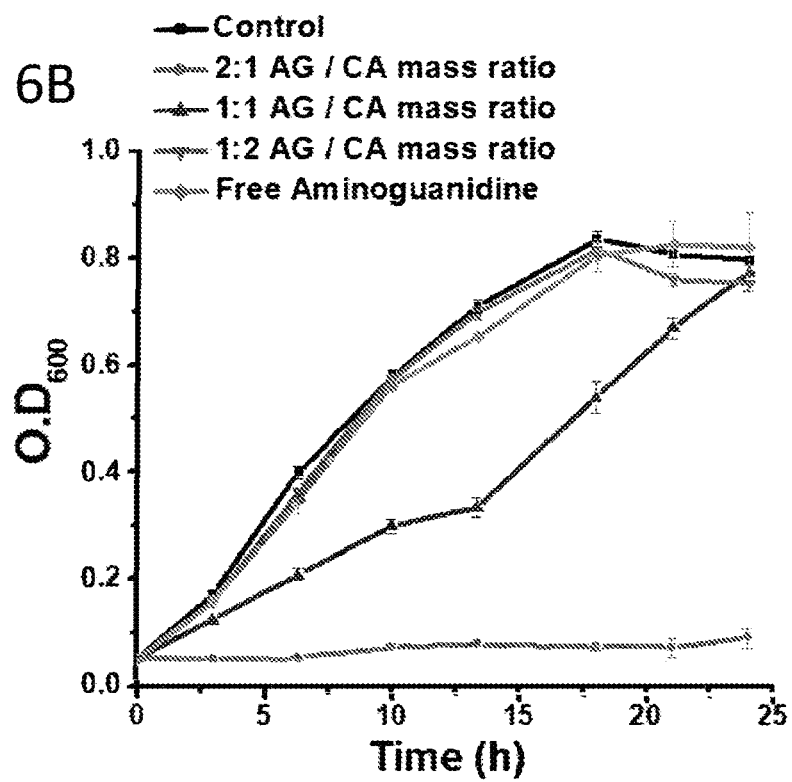
Figure 6C:
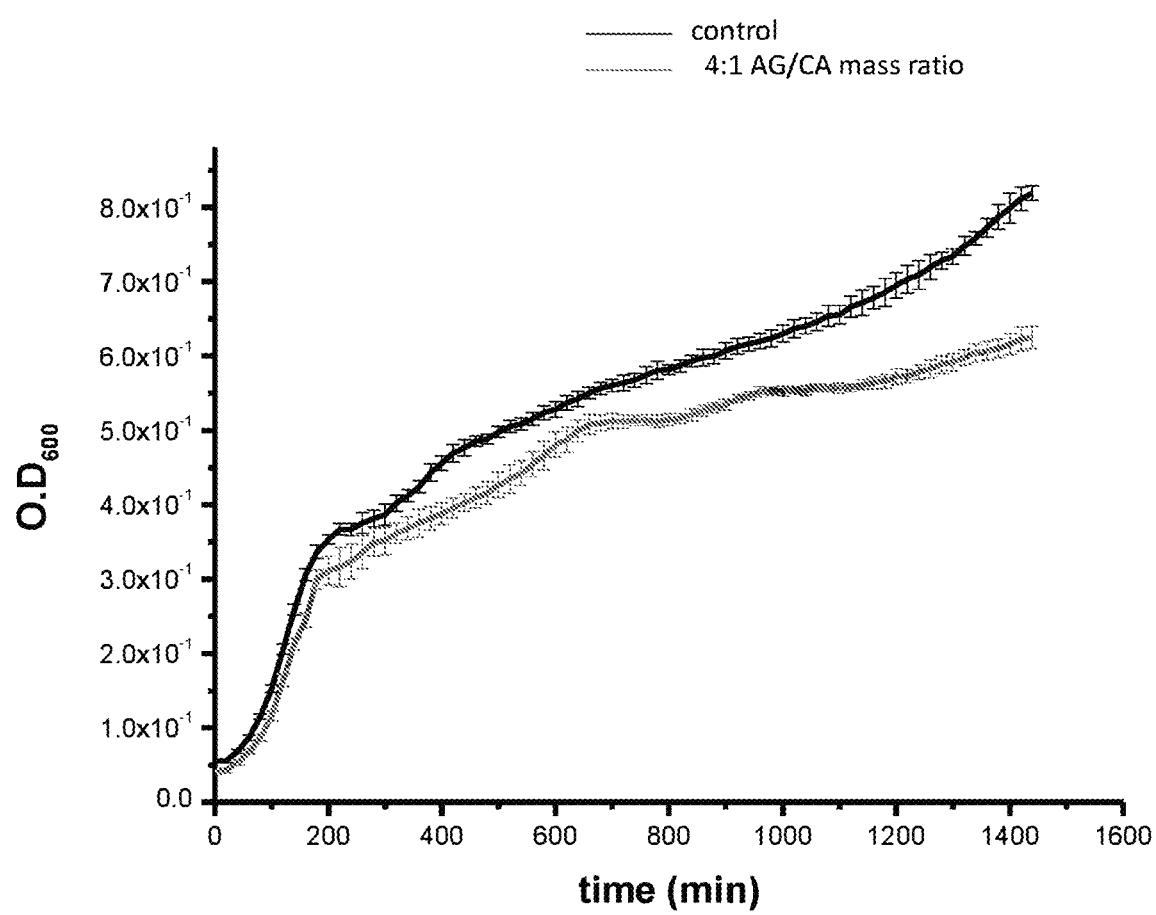

The effect that the C-dot surface groups composition has on their bactericidal activity was shown to be pronounced. As reported in section 1B herein above, C-dots having different mass ratios between the aminoguanidine and citric acid precursors were synthesized. Their corresponding antibacterial activity was assessed in p. aeruginosa cells. As can be seen in FIG. 6, the C-dots having a mass ratio of 2:1 (AG:CA) demonstrated an improved antimicrobial activity. As can be detected in FIG. 6A, there is a direct correlation between the content of nitrogen and the antibacterial activity over a certain rang, however, according to FIG. 6C, C-dots having a high ratio of 4:1. (AG:CA) demonstrated only a low antibacterial efficiency in comparison to C-tots having 2:1 ratio (FIG. 6B).

Example 3—Disruption to Biofilm Propagation

P. aeruginosa PAO 1 luxCDABE biofilm was grown in a clear glass bottom 96 well plate, typically through placing 300 μL of the medium in each well followed by addition of 5 μL bacterial solutions at $O.D_{600}$=1 (CFU=1×10$^8$). The resulting solution was grown for 24 hours in 37° C. to yield P. aeruginosa biofilms. The biofilm was washed several times by PBS buffer and imaged by confocal microscopy. In a similar manner, P. aeruginosa biofilm was grown in a medium containing 1 mg/mL of AG-CA-dots. The P. aeruginosa biofilm was imaged using confocal laser scanning microscopy (CLSM) Plan-Apochromat 20×/0.8 M27, Zeiss LSM880, Germany. Image processing to obtain 3-D images and to evaluate biofilm total volume was obtained using the IMAMS software (Bitplane, Zurich, Switzerland).

Results

Figure 4A:
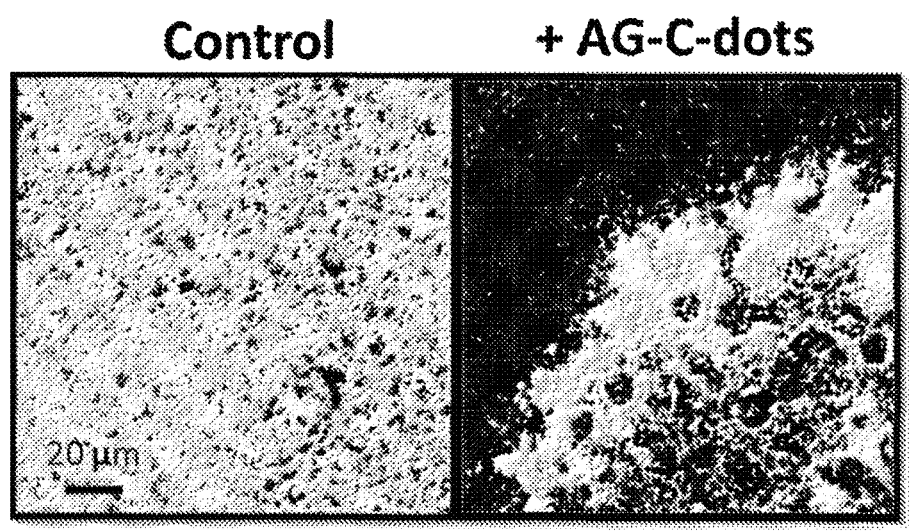
FIG. 4: Effect of the aminoguanidine carbon dots on *P. aeruginosa* biofilms. A. Brightfield confocal microscopy images of *P. aeruginosa* PAO 1 luxCDABE biofilm (24 hours growth) with and without incubation with AG-C-dots. B. Biofilm total volume (µm$^3$).
Figure 4B:
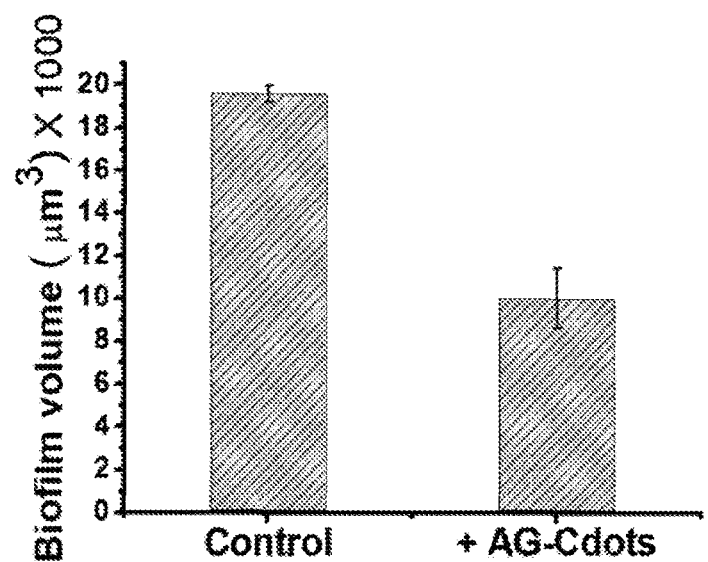

The microscopy images in FIG. 4 show a significant decrease in biofilm abundance when *P. aeruginosa* PAO 1 luxCDABE bacteria were incubated with the AG-C-dots for 24 hours. Biofilm volume determination, carried out by analysis of the three-dimension images, revealed close to 50% decrease upon AG-C-dots addition to the bacterial growth medium (FIG. 4B).

Example 4—Bacterial Cell Labeling

Bacterial cell labeling was conducted by initially growing all bacteria until full growth (O.D$_{600}$=1; CFU=1*10$^8$), followed by centrifugation of the bacterial solution and separation of the supernatant from the bacterial pellet. The bacterial pellet was washed several times by PBS buffer and then re-suspended in a solution of 1 mg/mL amino guanidine C-dots dissolved in PBS buffer. The resulting solution was incubated for 3 hours in 37° C. followed by washing of the bacterial pellet in PBS buffer in order to discard C-dots that were not attached to the bacteria. After final washing the C-dot-labelled bacterial pellets were re-suspended in PBS buffer and imaged by confocal laser scanning microscopy (CLSM) Plan-Apochromat 20×/0.8 M27, Zeiss LSM880, Germany.

Results

Figure 5:
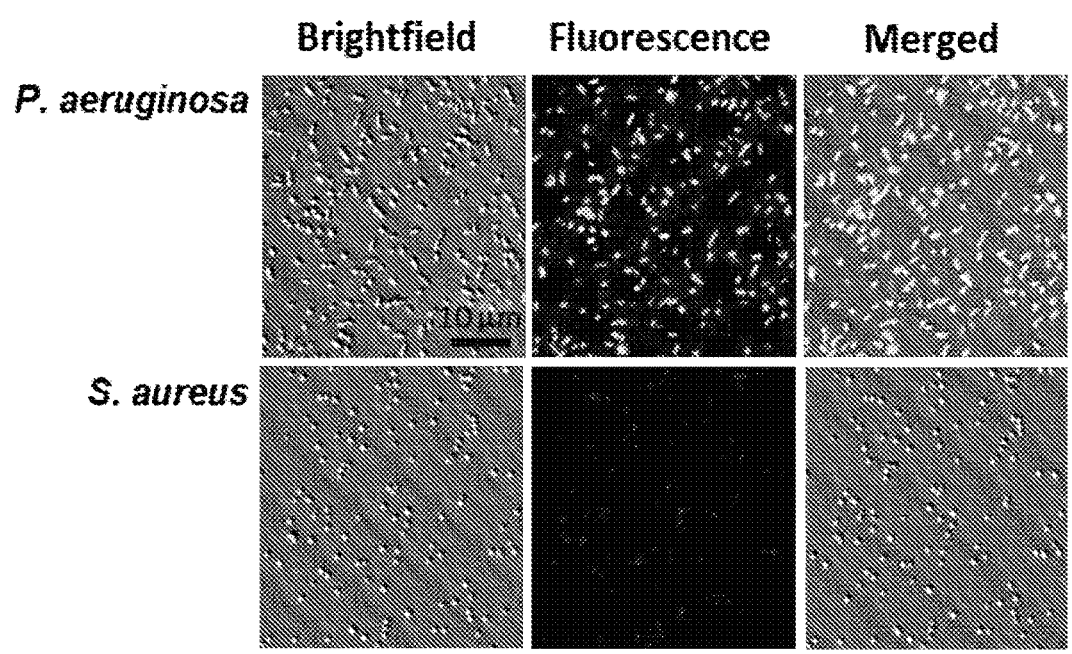
FIG. 5: Selective labelling of *Pseudomonas aeruginosa* by AG-C-dots. Confocal fluorescence microscopy images of *Pseudomonas aeruginosa* PAO 1 luxCDABE and *Staphylococcus aureus* by AG-C-dots 1 mg/mL, fluorescent images are presented with 405 nm excitation.

To accomplish bacterial cell staining, the bacterial suspensions were grown to saturation (OD600=1), pelleted, and incubated with the AG-C-dots (1 mg/mL) for 3 hours. The fluorescence microscopy images (excitation=405 nm) demonstrated that *P. aeruginosa* cells were labeled by the C-dots of the invention while no fluorescence labeling was apparent in case of *S. aureus*. The fluorescence microscopy results in FIG. 5 demonstrated the selectivity profile of the AG-C-dots, confirming specific targeting of *P. aeruginosa*. Furthermore, FIG. 5 demonstrates that bacterial staining (rather than killing) can be attained through tailoring the experimental parameters (C-dot concentration, point of C-dot addition to the bacterial suspension, and incubation time).

While the present disclosure has been illustrated and described with respect to a particular embodiment thereof, it should be appreciated by those of ordinary skill in the art that various modifications to this disclosure may be made without departing from the spirit and scope of the present disclosure.

What is claimed is:

1. Antimicrobial carbon-dots (C-dots) having at least one aminoguanidine functional group on their outer surface, wherein said C-dots are characterized in having a maximal emission at a wavelength of about 480 nm upon excitation at a wavelength of 390 nm, and wherein said antimicrobial C-dots inhibit the growth of *Pseudomonas aeruginosa*.

2. The antimicrobial C-dots according to claim 1, wherein said C-dots have a size between 3.5 and 5 nm in diameter.

3. The antimicrobial C-dots according to claim 1, wherein said C-dots are obtained by reacting a carboxylic acid with an aminoguanidine precursor, and wherein said C-dots are characterized by having an x-ray photoelectron spectrum (XPS spectrum) showing retention of the aminoguanidine and carboxylic acid residues by exhibiting:
   (a) a C1s spectrum featuring deconvoluted peaks at 284 eV, 285.2 eV, 286.5 eV, and 288.5 eV corresponding to C=C, C—N, C—O/C=N and C=O bonds; and
   (b) a N1s spectrum featuring deconvoluted peaks at 399.7 eV and 400.7 eV ascribed to C—N and C=N bonds.

4. The antimicrobial C-dots according to claim 1, wherein said C-dots are characterized by having quantum yield of about 3% in deionized water.

5. The antimicrobial C-dots according to claim 1, wherein said C-dots are characterized by having a zeta potential value higher than about −16 mV in phosphate-buffered saline (PBS buffer) at pH=7.4.

6. The antimicrobial C-dots according to claim 5, wherein said C-dots have a zeta potential between −1 to −15 mV in PBS buffer at pH=7.4.

7. The antimicrobial C-dots according to claim 6, wherein said C-dots have a zeta potential of about −2 mV in PBS buffer at pH=7.4.

8. The antimicrobial C-dots according to claim 6, wherein said C-dots have a zeta potential of about −2 mV in PBS buffer at pH=7.4.

9. A method for inhibiting the formation of a biofilm and/or disrupting the propagation of a biofilm comprising contacting antimicrobial C-dots having at least one aminoguanidine functional group on their outer surface with biofilm forming bacterial cells.

10. The method according to claim 9, wherein the bacterial cells are *Pseudomonas aeruginosa* cells.

11. The method according to claim 9, wherein the C-dots are characterized by having a zeta potential value higher than about −16 mV in PBS buffer at pH=7.4.

12. The method according to claim 11, wherein said C-dots have a zeta potential between −1 to −15 mV in PBS buffer at pH=7.4.

13. A method for selective bacterial cell labeling, comprising the steps of (A) contacting bacterial cells sought to be labeled with fluorescent C-dots having at least one aminoguanidine functional group on their outer surface at a concentration range of between about 0.1 mg/ml to about 1 mg/ml; and (B) removing excess C-dots; thereby providing precise cell labeling.

14. The method of claim 13, wherein the concentration of the bacteria in step (A) ranges between about OD$_{600}$ 0.1 to about 1.

15. The method of claim 14, wherein the aminoguanidine precursor is aminoguanidine hydrochloride.

16. A method for preparing antimicrobial C-dots having at least one aminoguanidine functional group on their outer surface, wherein said method comprises a step of reacting a carbonaceous molecule with an aminoguanidine precursor in aqueous media under heating, wherein a mass ratio between said aminoguanidine precursor and said carbonaceous molecule is between about 2.5:1 to about 1.5:1.

17. The method according to claim 16, wherein said carbonaceous molecule is selected from the group consisting of carboxylic acids, sugars, amino acids, ascorbic acid and peptides.

18. The method according to claim 16, wherein said carbonaceous molecule is a carboxylic acid.

19. The method according to claim 18, wherein the carbonaceous molecule is citric acid.

20. The method according to claim 19, wherein the mass ratio between aminoguanidine precursor to citric acid is about 2:1.

21. The method according to claim 16, wherein the heating occurs at a temperature of between about 120 to about 180 degrees Celsius.

22. An antimicrobial composition comprising C-dots having at least one aminoguanidine functional group on their outer surface, wherein said C-dots are characterized (i) in having a maximal emission at a wavelength of about 480 nm upon excitation at a wavelength of 390 nm, and wherein said antimicrobial C-dots inhibit the growth of *Pseudomonas aeruginosa*; or (ii) as prepared by a method according to claim 16.

\* \* \* \* \*